US00PP15055P3

(12) United States Plant Patent
Bradford

(10) Patent No.: US PP15,055 P2
(45) Date of Patent: Aug. 3, 2004

(54) NECTARINE TREE NAMED 'WESTERN SWEET'

(50) Latin Name: *Prunus persica*
Varietal Denomination: Western Sweet

(76) Inventor: Lowell Glen Bradford, 12439 E. Savana Rd., Le Grand, CA (US) 95333

( * ) Notice: Subject to any disclaimer, the term of this patent is extended or adjusted under 35 U.S.C. 154(b) by 263 days.

(21) Appl. No.: 10/302,975

(22) Filed: Nov. 25, 2002

(65) Prior Publication Data

US 2004/0103464 P1 May 27, 2004

(51) Int. Cl.[7] ..... A01H 5/00

(52) U.S. Cl. ..... Plt./192

(58) Field of Search ..... Plt./192

(56) References Cited

U.S. PATENT DOCUMENTS

| | | | |
|---|---|---|---|
| PP6,363 | P | 11/1988 | Bradford |
| PP7,193 | P | 3/1990 | Bradford |
| PP8,461 | P | 11/1993 | Bradford |
| PP11,954 | P2 | 6/2001 | Bradford |

*Primary Examiner*—Anne Marie Grunberg

(57) ABSTRACT

The present invention relates to a nectarine tree, *Prunus persica*, and more particularly to a new and distinct variety broadly characterized by a medium size, vigorous, hardy, self-fertile, productive and regular bearing tree. The fruit matures under the ecological conditions described in early July, with first picking on Jul. 7, 2002. The fruit is uniformly large in size, sub-acidic and sweet in flavor, slightly oblong in shape, freestone in type, firm in texture, yellow in flesh color, and mostly red in skin color. The variety was developed as a second generation cross using 'Red Glen' (U.S. Plant Pat. No. 7,193) yellow flesh nectarine as the selected seed parent and an unnamed white flesh freestone nectarine seedling as the selected pollen parent.

1 Drawing Sheet

Botanical classification: *Prunus persica.*
Variety denomination: 'Western Sweet'.

BACKGROUND OF THE VARIETY

In a continuing effort to improve the quality of shipping fruits, I, the inventor, typically hybridize a large number of peach, nectarine, plum, apricot, and cherry seedlings each year. I also grow a lesser number of open pollinated seedlings of each of these fruits, usually to capture the recessive traits. The present invention relates to a new and distinct variety of nectarine tree, which has been denominated varietally as 'Western Sweet'. In 1996 I gathered fruit from an unnamed nectarine seedling that was yellow in flesh color, sub-acidic in flavor, and freestone in type. The seeds were removed, stratified, germinated, and grown as seedlings on their own root in my greenhouse, and upon reaching dormancy transplanted to a cultivated area of my experimental orchard at Bradford Farms near Le Grand, Calif. in Merced County (San Joaquin Valley). During the fruit evaluation season of 1999 I selected the present variety as a single plant from the group described above. Specifically, the variety was developed as a second generation cross using 'Red Glen' (U.S. Plant Pat. No. 7,193) yellow flesh nectarine as the selected seed parent and an unnamed white flesh freestone nectarine seedling as the selected pollen parent. However, this unnamed pollen parent was itself a first generation cross using 'August Red' (U.S. Plant Pat. No. 6,363) yellow flesh nectarine as its selected seed parent and 'Bradcrim' (U.S. Plant Pat. No. 8,461) white flesh nectarine as its selected pollen parent. Subsequent to origination of the present variety of nectarine tree, I asexually reproduced it by budding and grafting in the experimental orchard described above, and such reproduction of plant and fruit characteristics were true to the original plant in all respects. The reproduction of the variety included the use of 'Nemaguard' (unpatented) rootstock upon which the present variety was compatible and true to type.

The present variety is similar to 'August Red', one of its selected pollen grandparents, by producing nectarines that are nearly globose in shape, yellow in flesh color, mostly red in skin color, and firm in texture but is quite distinguished therefrom by producing nectarines that are freestone instead of clingstone in type, sub-acidic instead of acidic in flavor, and mature about seven weeks earlier.

The present variety is similar to 'Bradcrim', the other selected pollen grandparent, by producing nectarines that are nearly globose in shape, freestone in type, and sub-acidic in flavor, but is quite distinguished therefrom by producing nectarines that are yellow instead of white in flesh color, larger in size, and mature about one week later.

The present variety is most similar to 'Grand Sweet' (U.S. Plant Pat. No. 11,954) nectarine, by producing nectarines that are very firm in texture, nearly full red in skin color, yellow in flesh color, and sub-acidic in flavor, but is distinguished therefrom by producing nectarines that are larger in size, freestone instead of clingstone in type, mature about 5 days earlier, and have a sweet instead of bitter kernel.

SUMMARY OF VARIETY

In summary, the present variety is characterized by a medium size, vigorous, hardy, self-fertile, productive and regular bearing tree. The fruit matures under the ecological conditions described in early July, with first picking on Jul. 7, 2002. The fruit is uniformly large in size, sub-acidic and sweet in flavor, slightly oblong in shape, freestone in type, firm in texture, yellow in flesh color, and mostly red in skin color.

DRAWING

The accompanying photograph exhibits four whole fruits positioned to display the characteristics of the skin color and form, one fruit divided along the suture plane to reveal the flesh and stone, and typical leaves.

POMOLOGICAL CHARACTERISTICS

Referring now more specifically to the pomological characteristics of this new and distinct variety of nectarine tree, the following has been observed under the ecological conditions prevailing near Le Grand, Merced County (San Joaquin Valley), Calif., and was developed at the state of firm ripe on Jul. 10, 2002, on the original tree during its sixth growing season. All major color code designations are by reference to the Inter-Society Color Council, National Bureau of Standards. Common color names are also used occasionally.

Tree

Size: Medium, reaching a height of 10' [3.05 m.] and a spread of 7' [2.13 m.] after six growing seasons utilizing typical dormant pruning.

Vigor: Vigorous, responding typically to irrigation and fertilization. The variety grows about 3' [0.91 m.] of surplus top-growth during the spring and summer. The plant should be grown on a standard commercial rootstock for production purposes.

Growth: Upright and dense.

Form: Vase formed.

Hardiness: Hardy with respect to central California winters.

Heat tolerance: Observed to perform adequately in typical central California climatic conditions, which typically include extended periods of heat.

Drought tolerance: Variety is developed for commercial orchards and requires regular irrigation.

Production: Productive, thinning necessary.

Fertility: Self-fertile.

Bearing: Regular bearer with no alternate bearing yet observed.

Trunk:

*Size.*—Medium, with a maximum diameter of 2½" [64 mm.] after the sixth growing season.

*Texture.*—Shaggy.

*Bark color.*—Grayish brown [61. gy.Br].

*Lenticels.*—Approximate Number Per Square Inch: 10. Color: Dark orange yellow [72. d.OY]. Average Size: 5/16" [7.9 mm.].

Branches:

*Size.*—Diameter of limb is 1 3/16" [30 mm.] measured 12" above the secondary scaffold, typical of *Prunus persica*, and dependent upon cultural practices and climatic conditions.

*Texture.*—Smooth on 1st year wood, increasing roughness with age.

*Color.*—1st Year Wood Topside: Moderate red [15. m.R]. 1st Year Wood Underside: Brilliant yellow green [116. brill.YG]. Older Wood: Deep yellowish brown [75. deep yBr].

*Lenticels.*—Approximate Number Per Square Inch: 75. Color: Light yellowish brown [76. l.yBr]. Typical size: 1/32" to 1/8" [0.8–3.2 mm.].

Leaves:

*Size.*—Medium. Average Length: 5⅜" [137 mm.]. Average Width: 1⅜" [35 mm.].

*Arrangement.*—Alternate.

*Thickness.*—Medium.

*Form.*—Elliptical.

*Apex.*—Acuminate.

*Base.*—Acute, with an average base angle of 80 degrees.

*Surface.*—Smooth.

*Color.*—Dorsal Surface: Moderate olive green [125. m.OlG]. Ventral Surface: Moderate yellow green [120. m.YG].

*Margin.*—Finely serrate.

*Venation.*—Pinnately net veined.

*Vein color.*—Light yellow green [119. l.YG].

*Petiole.*—Average Length: ⅜" [9.5 mm.]. Average Thickness: 1/16" [1.6 mm.]. Color: Brilliant yellow green [116. brill.YG].

*Stipules.*—Number: 2 per leaf, up to 4 per growing tip. Average Length: ⅜" [9.5 mm.]. Color: Strong yellow green [117. s.YG] becoming Grayish reddish brown [46. gy.rBr] when old.

*Glands.*—Average Number: 4. Position: Usually opposite, typically 2 on the petiole and 2 on the base of blade. Size: Small. Form: Appear to be globose when infant, but take on reniform shape with maturity. Color: Brilliant yellow green [116. brill.YG] on younger leaves acquiring Moderate reddish brown [43. m.rBr] centers with age.

*Leaf buds.*—Conic.

Flower buds:

*Hardiness.*—Hardy, with respect to central California winters.

*Diameter.*—Typically 5/16" [7.9 mm.] 1 week before bloom.

*Length.*—Typically ½" [12.7 mm.] 1 week before bloom.

*Form.*—Not appressed.

*Surface.*—Pubescent.

*Color.*—Moderate purplish pink [250. m.pPk].

Flowers: Perfect, complete, perigynous, usually a single pistil, typically thirty or more stamens, five sepals and petal locations alternately positioned.

*Type.*—Showy, large.

*Average flower diameter.*—1 13/16" [46.0 mm.].

*Number of petals.*—Usually five, double blossoms very rare.

*Petal shape.*—Circular.

*Petal margin.*—Somewhat wavy.

*Average petal diameter.*—¾" [19.1 mm.].

*Average petal length.*—⅞" [22.2 mm.].

*Petal apex.*—Rounded.

*Petal base.*—Rounded.

*Petal color.*—Pale pink [7. p.Pk].

*Anther color.*—Deep red [13. deep R] over a Light yellow [86. l.Y] center.

*Stigma color.*—Light greenish yellow [101. l.gY].

*Sepal color.*—Dark purplish red [259. d.pR].

*Sepal length.*—9/32" [7 mm.].

*Sepal width.*—3/16" [5 mm.].

*Average pistil length.*—⅝" [15.9 mm.].

*Average stamen length.*—9/16" [14.3 mm.].

*Fragrance.*—Moderate.

*Blooming period.*—Slightly early compared to other varieties.

*Onset of bloom.*—One percent on Mar. 1, 2002.

*Date of full bloom.*—Mar. 9 , 2002.

*Duration of bloom.*—One to two weeks, dependent on ambient temperature.

*Number per cluster.*—1 to 3 with single flowers most common.

FRUIT

Maturity when described: Firm ripe, Jul. 10, 2002.
Date of first picking: Jul. 7, 2002.
Date of last picking: Jul. 15, 2002.
Size: Uniform, large.
*Average diameter axially.*—3" [76.2 mm.].
*Average diameter across suture plane.*—2 15/16" [74.6 mm.].
*Typical weight.*—9.0 ounces [255 grams].
Form: Uniform, somewhat oblong, mostly symmetrical.
*Longitudinal section form.*—Elliptical, elongated axially.
*Transverse section through diameter.*—Circular.
Suture: A sharp groove from the stem to the shoulder, a shallow rounded trough along the side, and a deeper groove toward the apex that discontinues with a slight depression just beyond the pistil point.
Ventral surface: Rounded, lipped toward the apex on both sides.
Lips: Usually equal, sometimes unequal.
Cavity: Flaring, elongated in the suture plane, suture showing on one side, Light yellow [86. l.Y] stem markings typical.
*Depth.*—½" [12.7 mm.].
*Breadth.*—1⅛" [27.0 mm.].
Base: Rounded to somewhat truncate.
Apex: Rounded, cuneate when viewed along the suture.
Pistil point: Mostly apical, negligible in length, depressed within the suture.
Stem: Medium.
*Average length.*—⅜" [9.5 mm.].
*Average width.*—3/16" [4.8 mm.].
Skin:
*Thickness.*—Medium.
*Surface.*—Smooth.
*Tenacity.*—Tenacious to flesh.
*Astringency.*—Nonastringent.
*Tendency to crack.*—None observed in dry season.
*Color.*—Dark red [16. d.R] over a Strong reddish orange [35. s.rO] background with Brilliant orange yellow [67. brill.OY] freckling on the sides and the apex.
Flesh:
*Color.*—Vivid yellow [82. v.Y] with Moderate red [15. m.R] streaking close to the stone.
*Surface of pit cavity.*—Covered with Moderate reddish orange [37. m.rO] fibers cleanly releasing from the stone.
*Amygdalin.*—Scarce.
*Juice.*—Abundant, rich.
*Texture.*—Firm, crisp.
*Fibers.*—Abundant, fine.
*Ripens.*—Slightly earlier toward the apex and along the suture.
*Flavor.*—Sub-acid and very sweet, typically 18 to 21 brix.
*Aroma.*—Very slight.
*Eating quality.*—Very good.

STONE

Type: Freestone.
Form: Oval.
External color: Dark brown [59. d.Br].
Internal cavity color: Deep brown [56. deep Br].
Hilum: Narrow, oval.
Base: Straight.
Apex: Acute, with an average tip angle of 80 degrees.
Sides: Equal.
Surface: Irregularly furrowed near the apex and pitted toward the base.
Ridges: Jagged toward the base.
Average pit wall thickness: ¼" [6.4 mm.].
Average width: 1⅛" [27.0 mm.].
Average length: 1⅝" [41.3 mm.].
Average breadth: 13/16" [20.6 mm.].
Tendency to split: Slight.
Kernel:
*Form.*—Oval.
*Skin color.*—Light yellow [86. l.Y] when freshly removed.
*Pellicle color.*—Grayish yellowish brown [80. gy.yBr].
*Vein color.*—Light grayish yellowish brown [79. l.gy.yBr].
*Taste.*—Sweet.
*Viable.*—Yes.
*Average width.*—½" [12.7 mm.].
*Average length.*—13/16" [20.6 mm.].
*Amygdalin.*—Scant.

USE

Market: Fresh market and long distance shipping.
Keeping quality: Good. Fruit quality observed to remain in good condition after 21 days in standard cold room at 36° Fahrenheit [2° Celsius].
Shippinq quality: Good.
Resistance to insects: No unusual susceptibilities noted.
Resistance to diseases: No unusual susceptibilities noted.

Other Notes

Although the new variety of nectarine tree possesses the described characteristics under the ecological conditions at Le Grand, Calif., in the central part of the San Joaquin Valley, it is to be expected that variations in these characteristics may occur when farmed in areas with different climatic conditions, different soil types, and/or varying cultural practices.

I claim:

1. A new and distinct variety of nectarine tree, substantially as illustrated and described, that is most similar to 'Grand Sweet' (U.S. Plant Pat. No. 11,954) nectarine, by producing nectarines that are very firm in texture, nearly full red in skin color, yellow in flesh color, and sub-acidic in flavor, but is distinguished therefrom by producing nectarines that are larger in size, freestone instead of clingstone in type, mature about 5 days earlier, and have a sweet instead of bitter kernel.

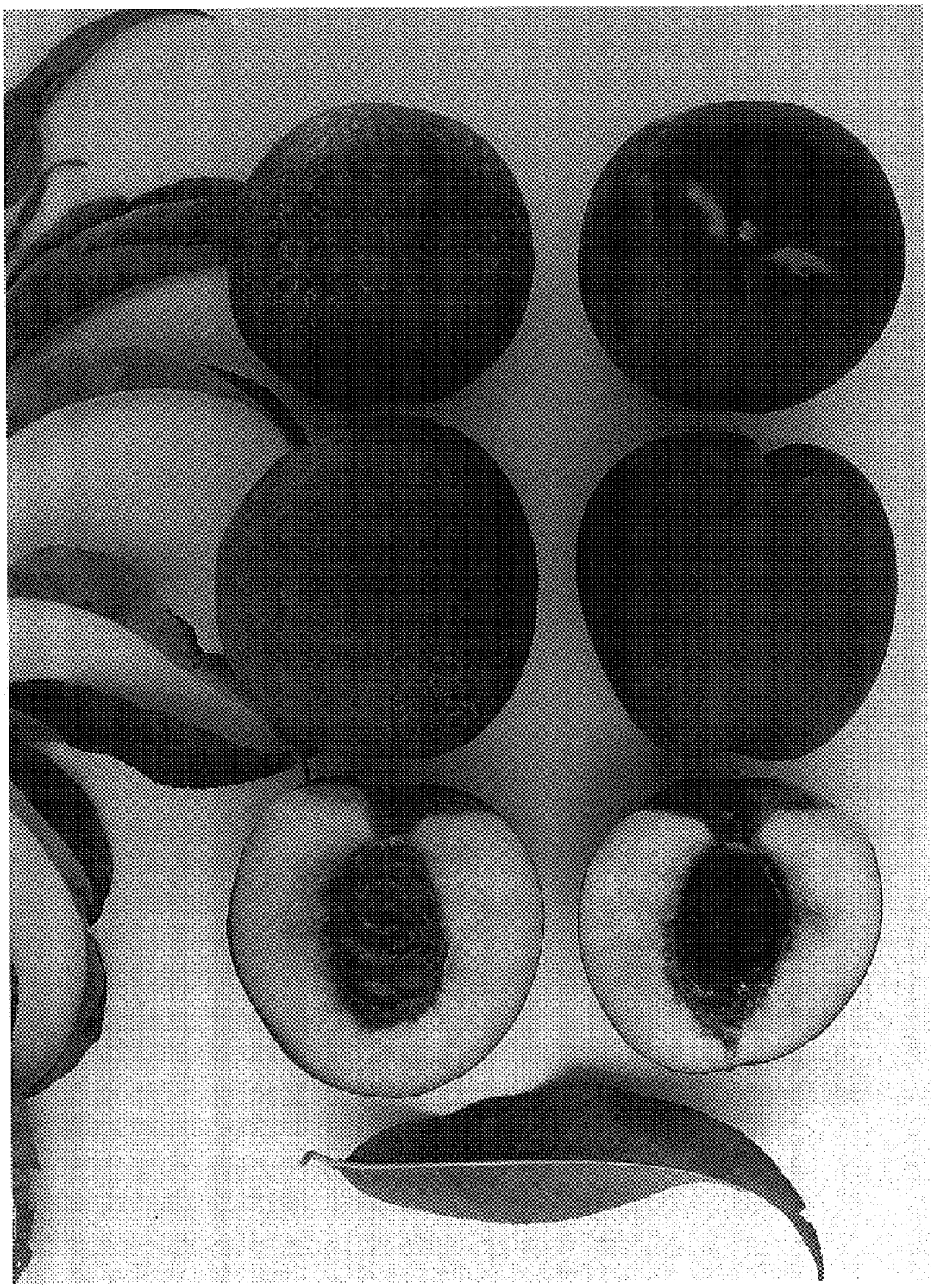

* * * * *